(12) United States Patent
Kobayashi

(10) Patent No.: US 8,529,879 B2
(45) Date of Patent: Sep. 10, 2013

(54) EPITHELIUM-IMPROVING AGENT

(75) Inventor: Haruzo Kobayashi, Takatsuki (JP)

(73) Assignee: Haruzo Kobayashi, Osaka (JP)

( * ) Notice: Subject to any disclaimer, the term of this patent is extended or adjusted under 35 U.S.C. 154(b) by 0 days.

(21) Appl. No.: 13/442,216

(22) Filed: Apr. 9, 2012

(65) Prior Publication Data

US 2012/0207728 A1    Aug. 16, 2012

Related U.S. Application Data

(62) Division of application No. 12/519,671, filed as application No. PCT/JP2008/053137 on Feb. 19, 2008, now abandoned.

(30) Foreign Application Priority Data

Mar. 13, 2007 (JP) ................. 2007-104316
Sep. 27, 2007 (JP) ................. 2007-279618

(51) Int. Cl.
*A61K 8/00* (2006.01)
*A61K 8/18* (2006.01)
*A61Q 5/00* (2006.01)
*A61Q 9/00* (2006.01)

(52) U.S. Cl.
USPC ........................................ 424/70.6; 424/70.1

(58) Field of Classification Search
None
See application file for complete search history.

(56) References Cited

U.S. PATENT DOCUMENTS

| 6,013,632 A | 1/2000 | Jones et al. |
| 6,726,932 B2 | 4/2004 | Konishi |
| 2004/0122109 A1 | 6/2004 | Fujii et al. |
| 2005/0277694 A1 | 12/2005 | Stock et al. |
| 2006/0134139 A1 | 6/2006 | Kurohashi et al. |
| 2008/0108699 A1 | 5/2008 | Tateishi et al. |

FOREIGN PATENT DOCUMENTS

| EP | 0645142 A1 | 3/1995 |
| JP | 57-106627 A | 7/1982 |
| JP | 02-059519 A | 2/1990 |
| JP | 11-228419 A | 8/1999 |
| JP | 2000-086504 A | 3/2000 |
| JP | 2002-332217 A | 11/2002 |
| JP | 2006-021997 A | 1/2006 |
| JP | 2006-306813 A | 11/2006 |
| JP | 2006-306832 A | 11/2006 |
| JP | 2007-008815 A | 1/2007 |
| JP | 2007-023015 A | 2/2007 |
| JP | 2007-153863 A | 6/2007 |
| WO | 02/02074 A2 | 1/2002 |
| WO | 2004/087167 A2 | 10/2004 |

OTHER PUBLICATIONS

Extended Search Report issued in corresponding European Patent Application No. 08720807.0 on Dec. 7, 2012.
Maurizio Battino et al., "Antioxidant status ($CoQ_{10}$ and Vit. E levels) and immunohistochemical analysis of soft tissues in periodontal diseases", BioFactors, 2005, 25: 213-217.
Anna Gvozdjakova et al., "Coenzyme $Q_{10}$ supplementation reduces corticosteroids dosage in patients with bronchial asthma", BioFactors, 2005, 25: 235-240.
T. Hanioka et al., "Effect of Topical Application of Coenzyme $Q_{10}$ on Adult Periodontitis", Molec. Aspects Med., 1994, 15(Supplement): s241-s248.
A. Koda et al., "Effect of Neurotropin (NSP) on Allergic Reactions", Nippon Yakurigaku Zasshi—Folia Pharmacologica Japonica, Nippon Yakuri Gakkai, 1981, 78(4): 319-334.
Milton Millman et al., "Use of Acetylcysteine in Bronchial Asthma—Another Look", Annals of Allergy, 1985, 54(4): 294-296.
Tetsuo Nakamoto et al., "The Role of Ascorbic Acid Deficiency in Human Gingivitis—A New Hypothesis", J. Theor. Biol., 1984, 108: 163-171.
Y. Yanagihara et al., "Immunopharmacological Actions of Neurotropin (3): Anti-Allergic Actions of Neurotropin", Nippon Yakurigaku Zasshi—Folia Pharmacologica Japonica, Nippon Yakuri Gakkai, 1981, 78(6): 589-597.
R. Eccles, "Efficacy and safety of over-the-counter analgesics in the treatment of common cold and flu", Journal of Clinical Pharmacy and Therapeutics, 2006, 31: 309-319.
A. Haerian et al., "Gingival crevicular stromelysin, collagenase and tissue inhibitor of metalloproteinases levels in healthy and diseased sites", Journal of Clinical Periodontology, 1995, 22: 505-509.
Margaret Hardy, "The secret life of the hair follicle", Trends in Genetics, 1992, 8(2): 55-61.
Hisamitsu Pharmaceutical Co., Inc., "Package Insert (L-cysteine preparation, Hythiol (Trademark) Powder 32%)", Apr. 2005.
M. Kylmaniemi et al., "Effects of Dexamethasone and Cell Proliferation on the Expression of Matrix Metalloproteinases in Human Mucosal Normal and Malignant Celle", Journal of Dental Research, 1996, 75(3): 919-926.
M. Makela et al., "Matrix Metalloproteinases (MMP-2 and MMP-9) of the Oral Cavity: Cellular Origin and Relationship to Periodontal Status", Journal of Dental Research, 1994, 73(8): 1397-1406.
T. Nemoto et al., "Ubidecarenon", Japanese Journal of Clinical and Experimental Medicine, 1997, 54(9): 3027-3029.
Y. Sagawa, et al., "Japanese Journal of Chest Diseases", 1985, 44(9): 774-782.

*Primary Examiner* — Jon P Weber
*Assistant Examiner* — Thane Underdahl
(74) *Attorney, Agent, or Firm* — Sughrue Mion, PLLC

(57) ABSTRACT

It is intended to provide an epithelium improving agent which improves the epithelial functions of various organs and, therefore, is usable in growing melanin-pigmented hair, relieving inflammatory symptoms in gingivitis and paradentitis, treating and relieving cold syndrome and bronchial asthma and, moreover, restoring sexual sensibility. An epithelium improving agent which comprises coenzyme Q10, cysteine, vitamins A, C and E and a skin extract of a rabbit inoculated with a vaccinia virus as the main components. In the case of treating gingivitis, paradentitis, cold syndrome and bronchial asthma, loratadine is further added. To an epithelium improving agent which is to be used in stimulating hair growth or restoring sexual sensibility, liquid paraffin and a hydrophilic ointment is further added to give a cream. Thus, the above problem can be solved.

9 Claims, 1 Drawing Sheet

EPITHELIUM-IMPROVING AGENT

CROSS-REFERENCE TO RELATED APPLICATIONS

Figure 1:
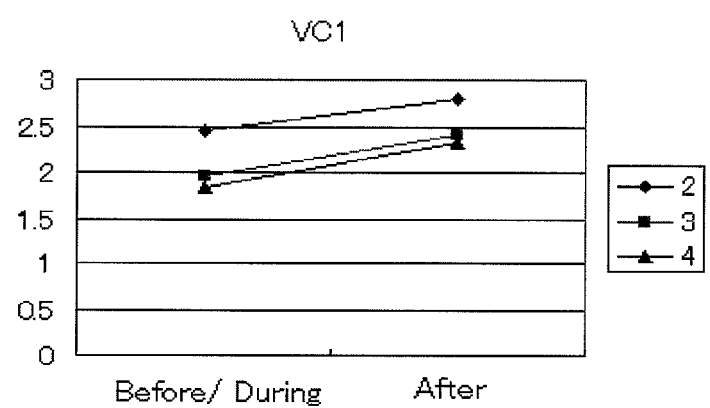

This is a divisional of U.S. patent application Ser. No. 12/519,671, filed Jun. 17, 2009, which is a 371 National Stage Entry of PCT/JP2008/053137, filed Feb. 19, 2008, and which claims benefit of JP 2007-104316, filed Mar. 13, 2007, and JP 2007-279618, filed Sep. 27, 2007. The entire disclosures of the prior applications are considered part of the disclosure of this continuing application and are hereby incorporated by reference.

TECHNICAL FIELD

The invention relates to an epithelium-improving agent having effects of;
1. improvement of inflammation of the gingival and periodontitis disease,
2. improvement of common cold,
3. improvement of bronchial asthma,
4. improvement of sexual sensation in the glans penis, clitoris, and vagina, and
5. hair growth which produces colored melanin-containing black hair in the area of white hair.

BACKGROUND ART

The gingival structure that supports the teeth is composed of the gingiva, alveolar bone, periodontal membrane, and dental cementum. Inflammation that is limited to the gingival area is classified as gingivitis, whereas inflammation that spreads from the gingiva to the alveolar bone, periodontal membrane, and dental cementum is classified as periodontitis. The treatment of gingivitis and more advanced periodontitis requires the removal of dental stains such as dental plaque and dental calculus, and the elimination of the cause of gingival swelling, if any, due to drug or pregnancy-induced endocrine stimulation. Effective methods include treatment with aminocaproic acid, which has anti-inflammatory action and anti-plasmin action on gingivitis and periodontitis, to inhibit the onset of such symptoms; the use of minocycline hydrochloride to eradicate tetracycline-resistant staphylococcus, which is a pathogen of periodontal inflammation; and the macrolide antibiotic, erythromycin, for the treatment of biofilm and pathogens in periodontal pockets. 60% of the periodontal tissue is composed of collagen. Continued collagen degeneration leads to gingival shrinkage and recession. The group of enzymes that act on and degrade extracellular matrices such as collagen are referred to as matrix metalloproteinases (hereinafter referred to as MMP). There are at least 10 types of MMP, among which collagenase is reportedly expressed around the attachment epithelia of the periodontal tissue and the periodontal pocket epithelia (see Non-Patent Document 1). It has also been reported that gelatinase is produced by epithelial cells through stimulation by periodontal pathogen-derived lipopolysaccharides and the like, and degrades type IV collagen, which is a constituent of the basement membrane. This shows that elevated MMP activity is intimately related to the progression of periodontal diseases. Normal individuals reportedly have lower levels of MMP than patients with gingivitis or periodontitis (see Non-Patent Document 2). Improvement of symptoms by treating periodontal diseases has also been reported to result in lower MMP activity (see Non-Patent Document 3). Agents for inhibiting the spread of gingival epithelial cells which contain plant extracts such as red grape, rosemary, ginkgo, St. John's wort, and alum are thus available to inhibit MMP activity and production (Patent Document 1). However, the above treatments currently do not afford adequate therapeutic results, and gingivitis often progresses to periodontitis, resulting in a loss of teeth in many individuals.

The common cold is caused by a virus. No drugs are effective for colds, and the only treatment is symptomatic treatment. Pseudoephedrine which is a decongestant is available for nasal discharge and nasal obstruction in colds, but its effects are limited. Oxymetazoline or phenylephrine nasal sprays are fast-acting, but their use is limited to a few days, as prolonged use may result in chronic nasal obstruction. Antihistamines and anti-allergy medication are available for nasal discharge, but side effects include sleepiness, and these types of medication are not effective for nasal obstruction. Centrally acting codeine and dextromethorphan are available for coughing. Codeine can result in nausea, vomiting, constipation, or tolerance and physical dependence. Respiratory depression is a side effect of higher doses of dextromethorphan. Palpitations, tremors, tachycardia, head ache, and vomiting are side effects of the bronchodilators, ephedrine and theophylline, which are not very effective anyway. N-(benzoyl)amino acid derivatives have recently become available for cough (Patent Document 2), but their clinical efficacy and side effects are still known. There is thus a need for a drug that would be effective and free of side effects even when used for longer periods of time.

Steroids, bronchodilating sympathetic drugs, anti-allergic agents, IgE neutralization therapy with anti-IgE antibodies, and ubidecarenone medication are effective for bronchial asthma (see Non-Patent Document 4), while effective therapies for respiratory diseases include those that are effective for dyspnea (see Non-Patent Document 5) and that are also effective on mast cells and eosinophils, such as dihomo-γ-linolenic acid (see Non-Patent Document 4), and the cysLT1 receptor antagonists pranlukast hydrate, montelukast sodium, and zafirlukast (Patent Document 5). Steroid inhalation therapy is currently the mainstream and has been shown to be effective in preventing death by asphyxiation due to bronchial asthma. However, the course of bronchial asthma is protracted, lasting from dozens of years to a lifetime, and the side effects of steroids are a problem. There is thus a need for a fast-acting drug that would be free of side effects, that would be as effective as or more effective than steroids, and that would be capable of long-term use.

Conventional impotence therapeutics for compromised sexual sensation in the glans penis, clitoris, and vagina are primarily in the form of oral medication, and their raw materials include extract of Trionychidae or garlic, powder or extract of Agkistrodon blomhoffii or Yohimbe bark, as well as maca and the like from the South American highlands. Testosterone transdermal absorption patches (Patent Document 6) and patches composed of stimulants such as chili pepper, capsaicin, or menthol have also recently become available (Patent Document 7), but there is a need for a drug that would be free of side effects, that would enhance the degree of sexual sensation in individuals with diminished sexual sensation, and that would be capable of long-term use.

Whiteing hair, hair loss, and thinning hair are a concern to people as they age. Whiteing hair is a phenomenon of aging, in which melanocytes stop producing melanin. The active ingredients of hair growth drugs include blood circulation stimulants, local stimulants, follicle activators, antiandrogens, antiseborrheics, keratolytics, bactericides, anti-inflammatories, and the like. Hair also repeatedly grows and falls out according to hair growth cycles. The formation of new follicles during the hair growth cycle is considered important to hair growth, at which time dermal papilla cells play a major role in follicle epithelial cell growth and differentiation as well as hair formation (Non-Patent Document 6). Extracts of astragalus root, Coptidis rhizome, and Wedelia chinensis are known examples of conventional drugs with action in stimulating dermal papilla cell growth, but there has yet to be provided a satisfactory hair growth agent that has action in stimulating dermal papilla cell growth, that has colored melanin-containing hair growth action, and that is free of side effects.

To deal with various types of external stress on the body (such as light, particularly UV rays, dust, exhaust gas, various chemical substances, and smoke) or bodily invasion by parasites or microbes such as viruses, bacteria, fungi, and protozoa, as well as antigen-induced allergic reactions, etc., these have conventionally been eradicated, or bactericides, fungicides, antibiotics, and the like have been used against microbes and parasites, and antibodies have been produced to develop resistance. However, until now, virtually no drugs have rehabilitated epithelial functions compromised by various external stimuli, by regenerating and stimulating the various epithelial functions which are most important in defending against external stimuli, microbial, parasitic, or other bodily invasion, and allergic responses, and which are the body's first inherent defense function against foreign threats. Furthermore, virtually no drugs rehabilitate epithelial functions by regenerating and stimulating the various epithelial functions that have become compromised as a result of aging. The inventor previously filed a patent application for a topical agent by the inventor which is applied to the skin to produce the four exceptional effects of making the skin smoother, healthier looking, fairer, and less wrinkled or unwrinkled with a single agent, as well as effects against atopic dermatitis. The topical agent by the inventor is furthermore effective against senile xerosis, frostbite, and housewives' eczema. Although the details of the mechanism involved in such effects remains unknown, the topical agent by the inventor may involve the effect of rehabilitating skin through the regeneration and stimulation of dermatological functions. Good therapeutic effects were found as a result of research on what kind of effect topical agents based on coenzyme Q10, cysteine, Vitamins A, C, and E, and an extract of inflamed skin from domestic rabbits inoculated with vaccinia virus, affording the beneficial effects on skin as noted above, would have on the epithelia of the ectodermal external auditory canal, nasal cavity, paranasal sinuses, oral cavity, and pharynx, on the epithelia of the endodermic tonsils, larynx, trachea, bronchi, and alveoli as well as mesodermic genital organs, which are all embryonically identical to skin, and also on hair, and what the effect would be when the epithelia of the above had aged and during pathological states. There is still a need for a drug that could be used over the long term to rehabilitate compromised epithelial functions through their regeneration and stimulation, and that could improve and rehabilitate aged or pathologically compromised epithelial functions.

[Patent Document 1] JP 2006-306832-A
[Patent Document 2] JP 2007-8815-A
[Patent Document 3] JP 2006-306813-A
[Patent Document 4] JP 2006-21997-A
[Patent Document 5] JP 11-228419-A
[Patent Document 6] JP 2000-86504-A
[Non-patent Document 1] M. Kylmaniemi, et al: J. Dent R s., 75, pp. 919-926 (1996)
[Non-patent Document 2] A. Haerian, et al: J. Clin Periodontol., 22 pp. 505-509 (1995)
[Non-patent Document 3] M. Makela, et a: J. Dent Res., 73, pp. 1397-1406 (1994)
[Non-patent Document 4] T. Nemoto, et al: Japanese Journal of Clinical and Experimental Medicine, vol. 54, 9 pp 3027-3029 (1977)
[Non-patent Document 5] Y. Sagawa, et al: The Japanese Journal of Chest Diseases, vol. 44, 9 pp 774-782 (1985)
[Non-patent Document 6] Trends Genet, 1992, vol. 8, pp 56-61

DISCLOSURE OF THE INVENTION

Problem to be Solved

The inventor previously filed a patent application (Patent Application 2005-380876) for a topical agent which is applied to the skin to produce the four exceptional effects of making the skin smoother, healthier looking, fairer, and less wrinkled or unwrinkled with a single agent, as well as effects against atopic dermatitis. Although the details of the mechanism involved in such effects remains unknown, this topical agent by the inventor may involve the regeneration and stimulation of dermatological functions. Research was conducted on what kind of effects an epithelium-improving agent based on coenzyme Q10, cysteine, Vitamins A, C, and E, and an extract of inflamed skin from domestic rabbits inoculated with vaccinia virus, affording the beneficial effects on skin as noted above, would have on the epithelia of the ectodermal external auditory canal which are all embryonically identical to skin, nasal cavity, paranasal sinuses, oral cavity, and pharynx, and on the epithelia of the endodermic tonsils, larynx, trachea, bronchi, and alveoli as well as the mesodermic genital organs, and also on hair, so as to provide an epithelium-improving agent that would be free of side effects, would improve the inflammatory symptoms of gingivitis and periodontitis, would improve the symptoms of the common cold and bronchial asthma, would restore sexual sensation, and would furthermore effectively grow hair, in order to improve pathology caused by various compromised epithelial functions.

Means of Solving the Problems

The present invention is an epithelium-improving agent which is based on coenzyme Q10, cysteine, Vitamins A, C, and E, and an extract of inflamed skin from domestic rabbits inoculated with vaccinia virus.

(1) Liquid epithelium-improving agent for inhalation by nebulizer to treat the common cold and bronchial asthma, Liquid epithelium-improving topical agent for application to treat gingivitis and periodontitis (using an interproximal brush), An epithelium-improving agent comprising coenzyme Q10 (0.03 to 1.2 weight parts), L-cysteine (0.48 to 2.4 weight parts), Vitamin A (0.06 to 0.36 weight parts), Vitamin C (2.0 to 8.0 weight parts), Vitamin E (0.4 to 1.6 weight parts), extract of inflamed skin from domestic rabbit inoculated with vaccinia virus 3.6 to 14.4 units and loratadine (0.01 to 0.12 weight parts) per 500 weight parts purified water. The liquid epithelium-improving agent for inhalation by nebulizer is diluted 3-fold with purified water at the time of use.

(2) Epithelium-improving agent in the form of an application cream for improving sexual sensation, and an epithelium-improving agent in the form of cream for application to grow hair, An epithelium-improving agent based on coenzyme Q10 (0.03 to 1.2 weight parts), L-cysteine (0.48 to 2.4 weight parts), Vitamin A (0.06 to 0.36 weight parts), Vitamin C (2.0 to 8.0 weight parts), Vitamin E (0.4 to 1.6 weight parts), extract of inflamed skin from domestic rabbit inoculated with vaccinia virus 3.6 to 14.4 units and liquid paraffin (4.4 to 13.2 weight parts) are used relative to 500 weight parts hydrophilic ointment as a topical agent for improving sexual sensation and hair growth.

Coenzyme Q10, L-cysteine, Vitamin A, Vitamin E, and loratadine in addition to Vitamin C and the extract of inflamed skin from domestic rabbits inoculated with vaccinia virus were used as preparation containing an additive, respectively, to ensure chemically stable interaction between the agents and to stabilize the epithelial absorption of the agents on the epithelium surface. The epithelium-improving agent where, with regard to the preparation additives, coenzyme Q10 ubidecarenone tablets (trade name Adelir Tablet 10) included lactose, crystalline cellulose, starch, carmellose calcium, hydroxypropyl cellulose, and magnesium stearate as additives;

L-cysteine powder (trade name Hithiol powder 32%) included lactose, glucose as additives;

Vitamin A retinol palmitate preparation (trade name Chocola A drops) included saccharin sodium, dibutyl hydroxytoluene, sodium dehydroacetate, butylhydroxyanisole, polyoxyethylene hydrogenated castor oil 60, perfume, a pH regulator as additives;

Vitamin E tocopherol nicotinate capsules (trade name NE soft capsule) included fatty acid ester of glycerin, gelatine, conc. glycerin, D-sorbitol, titanium oxide, propyl parahydroxybenzoate, yellow 5 as additives;

loratadine tablets (trade name Claritin tablets) included lactose, corn starch, magnesium stearate as additives.

Effect of the Invention

Using Method of Topical Agent of the Present Invention;

(1) for gingivitis and periodontitis, the epithelium-improving agent in the form of a gingivitis and periodontitis application liquid is interdentally applied using an interproximal brush, and (2) for the common cold and bronchial asthma, the epithelium-improving agent in the form of an inhalation liquid is inhaled with the use of an ultrasonic nebulizer into the nasal cavity, paranasal sinuses, oral cavity, pharynx, tonsils, larynx, trachea, bronchi, and alveoli.

(3) for improvement of sexual sensation, the epithelium-improving agent in the form of a sexual sensation-improving application cream is applied on the glans penis, clitoris, or vagina, and (4) for hair growth, the epithelium-improving agent in the form of a hair growth application cream is applied so as to be lightly rubbed into skin areas with white hair.

(I) Effect on Gingivitis and Periodontitis

Upon the interdental application of the inventor's gingivitis and periodontitis epithelium-improving agent using an interproximal brush for treatment of gingivitis and periodontitis, patients will be delighted by the rapid recovery from the pain, redness, and swelling, particularly the rapid relief of pain, associated with the inflammation of gingivitis and periodontitis. Loose teeth can also be improved if the periodontitis is mild, but may be slow to heal or may not improve if the periodontitis is severe. Prophylactic effects against periodontitis can therefore be expected with the sustained use of the gingivitis and periodontitis epithelium-improving agent using an interproximal brush before gingivitis develops into periodontitis, or while the area is inflammation-free and healthy, to prevent periodontitis. There was no recurrence of gingivitis or periodontitis after about one year or more in six out of 12 cases involving continuous interdental application of the gingivitis and periodontitis epithelium-improving agent using an interproximal brush.

The effect on gingivitis and periodontitis was investigated in 6 males and 6 females.

(1) A 69-year old female experienced pain, redness, swelling, and a loose left second mandibular molar on Aug. 23, 2006. After 7 days of application of the gingivitis and periodontitis epithelium-improving agent to the affected area and the application of the gingivitis and periodontitis epithelium-improving agent with the use of an interproximal brush to the affected area, the swelling and redness were relieved, and the pain was alleviated, with no local lymphatic pain. After 2 weeks, all pain was eliminated, and the loose tooth had improved by Oct. 4, 2006.

The patient also experienced pain, redness, and swelling in the right second mandibular molar tooth on Sep. 15, 2006, and the pain, redness, and swelling were cured with 10 days of similar treatment.

On Oct. 11, 2006, the patient also experienced pain, redness, swelling, and a loose left maxillary first premolar tooth. With similar treatment, pain was alleviated on the following day, symptoms of inflammation were resolved after 7 days, and the loose tooth improved. The patient experienced pain, swelling, and a loose right mandibular second molar tooth on Dec. 24, 2006. The application of the gingivitis and periodontitis topical agent to the affected area for three days resulted in pain relief as well as continuing improvement of the loose tooth.

No antibiotics and anti-inflammatory analgesics were used during that period, and investigation is currently ongoing regarding the prophylactic effects during subsequent continued use of the gingivitis and periodontitis epithelium-improving topical agent using an interproximal brush to prevent gingivitis and periodontitis. At present, as of August 2007, there has been no further pain, redness, or swelling, and the loose teeth continue to improve.

(2) 75-year old female experienced pain, redness, and swelling of the right mandibular first molar in September 2006, and the gingivitis and periodontitis epithelium-improving topical agent was applied to the affected area using an interproximal brush, eliminating the pain, redness and swelling in 4 days, with no recurrence after 3 months. No antibiotics and anti-inflammatory analgesics were used during that period, and investigation is currently ongoing regarding the prophylactic effects during continued use of the gingivitis and periodontitis epithelium-improving topical agent using an interproximal brush to prevent gingivitis and periodontitis. As of January 2008, there had been no further dental pain, redness, or swelling.

(3) A 55-year old male had undergone extraction of the left maxillary first molar due to periodontitis two years previously. On Sep. 14, 2006, he experienced pain, redness, and swelling of the right maxillary first molar similar to that 2 years previously. With the application of the gingivitis and periodontitis epithelium-improving topical agent to the affected area using an interproximal brush, pain was alleviated in 7 days, while the pain, redness, and swelling were fully cured on Oct. 11, 2006. No antibiotics and anti-inflammatory analgesics were used during that period. Investigation is currently ongoing regarding the prophylactic effects during subsequent continued use of the gingivitis and periodontitis epithelium-improving topical agent using an interproximal brush to prevent gingivitis and periodontitis. As of January 2008 there had been no recurrence of gingivitis or periodontitis.

(4) A 62-year old female experienced pain, redness, and swelling of the right mandibular second molar, and the gingivitis and periodontitis epithelium-improving topical agent was applied to the affected area using an interproximal brush, alleviating the pain in 4 days and totally curing the pain, redness, and swelling in 7 days. No antibiotics and anti-inflammatory analgesics were used during that period.

(5) A 49-year old male experienced pain, redness, and swelling of the right maxillary second molar, and the gingivitis and periodontitis epithelium-improving topical agent was applied to the affected area using an interproximal brush, curing the pain, redness, and swelling in 5 days. An anti-inflammatory analgesic was used, but no antibiotics were used.

(6) An 80-year old male had lost 12 teeth due to periodontitis between the age of 60 to 70 years. In September 2006, the patient experienced pain, redness, and swelling of the right mandibular canine, and the tooth was very loose. After 7 days of application of the gingivitis and periodontitis epithelium-improving topical agent to the affected area and the application of the gingivitis and periodontitis epithelium-improving topical agent with the use of an interproximal brush to the affected area, the pain, redness and swelling were relieved, and the tooth was no longer loose, allowing the patient to eat even hard foods. The right mandibular molar was also painful and loose. Two months of the above treatment resulted in total pain relief, but the right mandibular second molar fell out, perhaps because the pathology was so old. Investigation is currently ongoing regarding the prophylactic effects during subsequent continued use of the gingivitis and periodontitis epithelium-improving topical agent using an interproximal brush to prevent gingivitis and periodontitis. As of January 2008 there had been no recurrence of gingivitis or periodontitis.

(7) A 76-year old female had had for some time (date unknown) been experiencing pain, redness, and swelling of the right maxillary canine, and the tooth was very loose. Starting on Oct. 11, 2006, the periodontitis topical agent was applied to the affected area using an interproximal brush, alleviating the pain in 3 to 4 days, and completely eliminating the pain, redness, and swelling after 1 month, with some improvement of the dental looseness. No antibiotics and anti-inflammatory analgesics were used during that period. Investigation is currently ongoing regarding the prophylactic effects during subsequent continued use of the inventor's topical agent using an interproximal brush to prevent gingivitis and periodontitis. As of January 2008 there had been no recurrence of gingivitis or periodontitis.

(8) A 62-year old female experienced pain, redness, and swelling of the right mandibular lateral incisor, and the tooth was very loose. Starting on Oct. 7, 2006, the gingivitis and periodontitis epithelium-improving topical agent was applied to the affected area using an interproximal brush, relieving the pain, redness, and swelling in 3 to 4 days, but the looseness of the tooth failed to improve after 7 days. Treatment is currently ongoing. No antibiotics and anti-inflammatory analgesics were used during that period.

(9) A 57-year old male experienced pain, redness, and swelling of the right maxillary molar, and the gingivitis and periodontitis epithelium-improving topical agent was applied to the affected area using an interproximal brush, relieving the pain, redness, and swelling in 4 days. No antibiotics and anti-inflammatory analgesics were used during that period. The gingivitis and periodontitis epithelium-improving topical agent was not subsequently used.

(10) A 60-year old female had experienced pain, redness, and swelling of the right mandibular second molar since August 2006. She had visited a dentist six times by October 2006. Although the symptoms had been relieved at that time, the patient experienced bleeding, pain, redness, and swelling in the right mandibular second molar in October of that year. Application of the gingivitis and periodontitis epithelium-improving topical agent to the affected area using an interproximal brush relieved the pain, redness, and swelling in 5 days. No antibiotics and anti-inflammatory analgesics were used during that period. With subsequent continued use of the gingivitis and periodontitis epithelium-improving topical agent, there was no recurrence as of August 2007, but in August the patient experienced pain in the right mandibular second molar, and the frequency of the application of the epithelium-improving topical agent to the affected area using the interproximal brush was subsequently increased, with no pain, redness, or swelling as of January 2008. Use of the gingivitis and periodontitis epithelium-improving topical agent with the use of an interproximal brush and a tooth brush to prevent gingivitis and periodontitis is ongoing. From October 2006 to January 2008, the patient visited a dentist one time in August 2007.

(11) An 84-year old male visited a dentist, complaining of pain, redness, and swelling of the right mandibular first premolar in January 2006. The patient was told the tooth might fall out and was treated, but the pain, redness, and swelling persisted. Application of the gingivitis and periodontitis epithelium-improving topical agent to the affected area using an interproximal brush resulted in pain relief in about half a day, with alleviation of the redness and swelling. No antibiotics and anti-inflammatory analgesics were used during that period.

(12) A 92-year old female experienced pain, redness, and swelling of the right maxillary first premolar in January 2006, and the gingivitis and periodontitis epithelium-improving topical agent was applied to the affected area using an interproximal brush, relieving the pain in 3 days. Treatment is currently ongoing. No antibiotics and anti-inflammatory analgesics were used during that period. Use of the gingivitis and periodontitis epithelium-improving topical agent with the use of an interproximal brush to prevent gingivitis and periodontitis is ongoing.

(II) Effect on the Common Cold (A) Effect of Single Ultrasonic Nebulizer Inhalation Treatment with Inhalation Epithelium-Improving Topical Agent The effect on the symptoms of the common cold was studied in 61 patients (22 males and 39 females). Prior to cold medication, the inhalation epithelium-improving topical agent was diluted 3-fold with purified water at the time of use, and the effect resulting from just a single 10-min inhalation treatment using an ultrasonic nebulizer was investigated immediately after inhalation.

(1) Chills: Four of the 61 patients experienced chills. The medication was not effective in 2, and the effect was unknown in 2.

(2) Head ache: Twelve of the 61 patients experienced head aches. The medication was effective in 1 patient, somewhat effective in 3, and not effective in 5, while the effect was unknown in 3.

(3) Myalgia: Thirteen of the 61 patients experienced myalgias. The medication was somewhat effective in 2 patients, and not effective in 7, while the effect was unknown in 4.

(4) Fatigue: Thirty of the 61 patients experienced fatigues. The medication was effective in 5 patients, somewhat effective in 2, and not effective in 15, while the effect was unknown in 8.

(5) Sneeze: Fifteen of the 61 patients experienced sneezes. The medication was effective in 3 patients, somewhat effective in 7, and not effective in 1, while the effect was unknown in 4.

(6) Nasal itching: Eighteen of the 61 patients experienced nosal itchings. The medication was effective in 8 patients, somewhat effective in 8, while the effect was unknown in 2.

(7) Nasal discharge: Twenty eight of the 61 patients experienced nosal discharges. The medication was effective in 12 patients, and not effective in 3, while the effect was unknown in 1.

(8) Nasal obstruction: Twenty nine of the 61 patients experienced nasal obstructions. The medication was effective in 15 patients, somewhat effective in 11, and not effective in 3, while the effect was unknown in 0.

(9) Dry pharynx: Twenty one of the 61 patients experienced dry pharynxs. The medication was effective in 6 patients, somewhat effective in 8, and not effective in 5, while the effect was unknown in 2.

(10) Sore throat: Forty six of the 61 patients experienced sore throats. The medication was effective in 21 patients, somewhat effective in 14, and not effective in 6, while the effect was unknown in 5.

(11) Cough: Forty three of the 61 patients experienced coughs. The medication was effective in 18 patients, somewhat effective in 17, and not effective in 4, while the effect was unknown in 4.

(12) Hoarseness: Thirteen of the 61 patients experienced hoarsenesses. The medication was effective in 2 patients, somewhat effective in 2, and not effective in 6, while the effect was unknown in 3.

Effect of treatment with inhalation epithelium-improving topical agent:

| | Sympthom | Patients Number | Effective | Somewhat Effective | Not Effective | Un-known |
|---|---|---|---|---|---|---|
| 1 | Chills | 4/61 | 0 | 0 | 2 | 2 |
| 2 | Head ache | 12/61 | 1 | 3 | 5 | 3 |
| 3 | Myalgia | 13/61 | 0 | 2 | 7 | 4 |
| 4 | Fatigue | 30/61 | 5 | 2 | 15 | 8 |
| 5 | Sneeze | 15/61 | 3 | 7 | 1 | 4 |
| 6 | Nasal itching | 18/61 | 8 | 8 | 0 | 2 |
| 7 | Nasal discharge | 28/61 | 12 | 12 | 3 | 1 |
| 8 | Nasal obstruction | 29/61 | 15 | 11 | 3 | 0 |
| 9 | Dry pharynx | 21/61 | 6 | 8 | 5 | 2 |
| 10 | Sore throat | 46/61 | 21 | 14 | 6 | 5 |
| 11 | Cought | 43/61 | 18 | 17 | 4 | 4 |
| 12 | Hoarseness | 13/61 | 2 | 2 | 6 | 3 | was obtained.

The use of the inhalation epithelium-improving topical agent for the common cold in a single 10-min inhalation treatment using an ultrasonic nebulizer was effective for particularly severe symptoms when inhaled, and demonstrated considerable fast-acting effect for nasal discharge, nasal obstruction, sore throat, cough, and the like. Inhalation of the inhalation epithelium-improving topical agent 3 to 4 times a day by ultrasonic nebulizer every time symptoms occur, if possible, may be even more effective.

(B) Treatment of Common Cold by Inhalation of Inhalation Epithelium-Improving Topical Agent Alone 1. A 13-year old male presented with a fever of 37.0° C., fatigue, dry pharynx, sore throat, dry spasmodic cough, sneezing, itching sensation in nose, nasal discharge, and nasal obstruction. The patient visited on Day 2 of onset, and 10-min of treatment with the inhalation epithelium-improving topical agent by ultrasonic nebulizer was effective for the nasal obstruction and cough. Treatment 3 hours later and once the next morning, for a total of three inhalation treatments, resulted in abatement of fever, relief from the cold symptoms, and full recovery 3 days after onset. No antipyretics and cold medication were used.

2. A 47-year old female presented with a normal temperature of 36.4° C., fatigue, itchy throat, nasal discharge, and nasal obstruction. The patient visited on Day 2 of onset. The first 10-min inhalation treatment with the inhalation epithelium-improving topical agent by ultrasonic nebulizer was effective for the nasal obstruction on one side. The nasal discharge was also stopped, although the effect on the throat was unknown. After about 3 hours, the above symptoms abated, and the patient felt fully recovered. After 7 hours, the patient experienced an itchy throat and nasal obstruction, and a second similar 10-min inhalation treatment resulted in improvement of the above symptoms. The patient experienced a sore throat the next day. After a third similar 10-min inhalation treatment, the sore throat felt better. On Day 4 of onset, symptoms abated, and the patient had fully recovered 4 days after onset.

3. A 52-year old female presented with fatigue, dry feeling in the throat, sore throat, sneezing, and chills, but a body temperature of 36.8° C. Three 10-min treatments with the inhalation epithelium-improving topical agent by ultrasonic nebulizer over 3 days resulted in improvement of the above symptoms and in full recovery 4 days after onset.

4. A 41-year old female presented with a normal temperature of 36.6° C., fatigue, cough, nasal discharge, and nasal obstruction. 10-min of treatment with the inhalation epithelium-improving topical agent by ultrasonic nebulizer was effective for the nasal obstruction and somewhat effective for the cough and nasal discharge. Three inhalation treatments with the epithelium-improving topical agent by ultrasonic nebulizer, once a day for three days, resulted in full recovery in 3 days.

5. A 70-year old female presented with fatigue, itchy throat, cough, and chills, but a temperature of 35.4° C. The first 10-min treatment with the inhalation epithelium-improving topical agent by ultrasonic nebulizer was effective for the sore throat. Three inhalation treatments with the epithelium-improving topical agent by ultrasonic nebulizer, once a day for three days, resulted in full recovery in 3 days.

6. A 63-year old female complained of feeling as if she had caught a cold and a sore throat. 10-min of treatment with the inhalation epithelium-improving topical agent by ultrasonic nebulizer resulted in improvement of the sore throat, and three inhalation treatments with the epithelium-improving topical agent by ultrasonic nebulizer, once a day for three days, resulted in full recovery in 3 days.

7. A 66-year old female had caught a cold 2 days before, and visited while suffering from a severe cough. She was treated with the inhalation epithelium-improving topical agent by ultrasonic nebulizer. The single inhalation treatment with the inhalation epithelium-improving topical agent by ultrasonic nebulizer stopped the cough and resulted in full recovery in 3 days.

8. One year and two-month old female (1) The patient's visit was preceded by onset of nasal discharge 7 days before and by cough 2 days before. On visiting, the patient presented with a temperature of 38.5° C., nasal discharge, and cough. A 10-min episode of inhalation of the inhalation epithelium-improving topical agent by ultrasonic nebulizer was effective for the nasal discharge and cough. The fever returned to normal temperature, without any antipyretics or cold medication, with deep sleep for about 4 hours. No cold medication or antipyretics were used in that period, and the same 10-min inhalation treatment was the only treatment. The patient visited 3 days later, with normal temperature, cough, and nasal discharge. A 10-min inhalation treatment was effective for the cough and nasal discharge, and the patient had fully recovered in 4 days after visiting.

(2) The patient had a cough and nasal discharge for 3 days. On the morning of the patient's visit, body temperature was 37.5° C. A 10-min inhalation treatment for symptoms of the common cold was effective for the cough and nasal discharge, and the patient subsequently slept well. The patient had a fever of 39.1° C. at 5 PM. The patient visited again, and after 10 min of inhalation treatment, the temperature fell to 38.4° C. At the second visit, the morning body temperature was 36.8° C. In the early evening, body temperature was 37.8° C., and the patient was treated by the same 10-min inhalation treatment. At the 3rd visit on the following day, the fever had abated and symptoms were resolved. The patient fully recovered 6 days after visiting. No antipyretics were used in that time. The patient was also treated with cefpodoxime proxetil for tonsillitis.

9. A 52-year old male presented with a scratchy throat, itchy nose, obstruction, temperature of 35.8° C., and bilateral submandibular lymph node tenderness. 10-min treatments with the epithelium-improving topical agent by ultrasonic nebulizer once on Day 1 and twice on Day 2 (morning and evening), for a total of three times, each resulted in relief of the symptoms of sore throat, itchy nose, nasal obstruction, and submandibular lymph node tenderness, with full recovery 3 days after visiting.

10. A 3-year old female had a cough and nasal discharge since the previous evening, but no fever. When the patient visited, her temperature was 37.3° C. A 10-min inhalation treatment with the inhalation epithelium-improving topical agent by ultrasonic nebulizer was effective for the cough and nasal discharge. Upon her return home, her fever fell, she played normally, and she recovered by the following day.

(C) Effect of the Epithelium-Improving Topical Agent on Fever Among Symptoms of the Common Cold when Inhaled by Ultrasonic Nebulizer (1) Treatment of the 13-year old male in part 1. of section (B) with the epithelium-improving topical agent by three inhalation treatments with an ultrasonic nebulizer over 2 days resulted in a decrease from a fever of 37.0° C. to normal temperature as well as in relief of, and recovery from, symptoms of the common cold.

(2) After treatment of the 1-year 2-month old female in part 8. of section (B) with the epithelium-improving topical agent by a single treatment with an ultrasonic nebulizer, the fever of 38.5° C. returned to normal after 4 hours without any antipyretics or cold medication.

(3) An 8-year old male had a temperature of 38.3° C. on the day before visiting. At the patient's visit, the temperature was 37.9° C., and the patient complained of a head ache and fever. After 10-Min of treatment with the inhalation epithelium-improving topical agent by ultrasonic nebulizer, the head ache improved. After 1 hour, the temperature was 37.3° C., and the temperature was normal the next day. The patient went to school in good health. No antipyretics were used in that time.

(4) A 3-year old female had a fever over 39.0° C. at 8 PM the day before visiting, and was given an antipyretic suppository. Around 2 AM on the day of the patient's visit, the patient again had a high fever and was given another suppository. Upon visiting (12 PM), the patient was limp, with a temperature of 38.0° C., nasal discharge, nasal obstruction, severe cough, and dry rales on chest auscultation. 10-min of treatment with the epithelium-improving topical agent by ultrasonic nebulizer was effective for the nasal discharge, nasal obstruction, and cough. The patient's mood improved enough to begin reading a waiting room book. The patient visited in good spirits with a temperature of 37.8° C. at 6 PM on the same day. The cough and nasal obstruction were resolved, and only the nasal discharge remained. After the same 10-min inhalation treatment, the fever abated that same day. Apart from only a slight cough on the following day, the patient had fully recovered.

(D) Effect of Long-Term Inhalation of Epithelium-Improving Topical Agent by Ultrasonic Nebulizer on Common Cold A 1-year and 8-month old female was susceptible to catching cold, leading to bronchial asthma. The patient visited in April 2007, and subsequently visited 3 to 6 times a month with colds and bronchial asthma. Starting on Sep. 14, 2007, the patient began daily treatments with the epithelium-improving topical agent by ultrasonic nebulizer for 10 min once a day at home, during which time she contracted chicken pox on Oct. 7, 2007 and suffered a mild asthma attack, but recovered using the same inhalation treatment, and then contracted a cough in early November 2007, but recovered in 2 days using the same inhalation treatments, with no subsequent colds or asthma attacks. She has continued to use inhalation treatment once every 2 to 3 days, and has been in good health, with no visits for 3 and a half months so far at the end of December. On Jan. 14, 2008, she contracted influenza type A, but suffered no bronchial asthma attacks and recovered in about 4 days.

(III) The Effect on Bronchial Asthma was Investigated in 3 Males and 4 Females.

(1) A 63-year old female had been suffering from asthma attacks and allergic rhinitis for the last four years since about the age of 59-years. Until her visit in January 2006, she had been treated with fluticasone propionate, pranlukast hydrate, and theophylline, as well as antibiotics, antitussives, and expectorants, but constantly suffered from coughing, phlegm, wheezing, and dyspnea, and experienced asthma attacks from time to time. Treatment failed to improve symptoms, and her condition has fluctuated for 4 years. At the patient's visit on Jan. 31, 2006, she had a cough, expectorated sputum, suffered from dyspnea, and exhibited dry rales on chest auscultation. Oral and topical medication included:

Montelukast sodium 10 mg tablet: 1 tablet
Epinastin hydrochloride 20 mg tablets: 1 tablet
Betamethasone 0.5 mg tablets: 2 tablets (initially, twice in the morning and evening, then reduced to once in the evening, and kept on hand for emergencies in the absence of attacks)
Procaterol hydrochloride: 2 inhalations, up to 4 times, daily
Fluticasone propionate inhalation: twice daily Feb. 20, 2006: Although severe attacks had abated, the patient experienced mild dyspnea, coughing, and expectorated sputum. Chest auscultation revealed dry rales. She had stopped taking betamethasone tablets but kept some on hand for emergencies.

On Feb. 20, 2006, the patient started taking 1 mL of the inhalation epithelium-improving topical agent and 2 mL of sodium cromoglicate inhalation liquid by ultrasonic nebulizer 2 to 3 times a day.

The patient started inhalation of fluticasone propionate once a day on Apr. 18, 2006 and stopped on Jun. 2, 2006. The patient has been completely free of asthma since the beginning of June, and chest findings have been normal.

Since Oct. 24, 2006, the patient has continued to use 1 mL of the inventor's inhalation epithelium-improving agent by ultrasonic nebulizer once or twice a day, with no symptoms of asthma until December 2006, but suffered a mild asthma attack on December 12, perhaps because she was unable to use the inhalation epithelium-improving agent for 5 days while travelling. The asthma was cured in 2 days by treatment with procaterol hydrochloride, sodium cromoglicate, and the inhalation epithelium-improving agent of the invention. The patient was subsequently asthma-free while being treated using only the inhalation epithelium-improving topical agent, but sustained a contusion of the right brachia in January 2007 and stopped taking the inhalation epithelium-improving topical agent for 7 days, leading to another mild attack of asthma. The asthma was cured in 3 days by treatment with procaterol hydrochloride, sodium cromoglicate, and the inhalation epithelium-improving agent of the invention. The patient was subsequently asthma-free until August 2007 while being treated using only the inhalation epithelium-improving topical agent. The fact that discontinuation of the inhalation epithelium-improving topical agent during treatment for bronchial asthma resulted in asthma attacks showed that inhalation of the inhalation epithelium-improving topical agent by ultrasonic nebulizer was effective for bronchial asthma.

(2) An 80-year old male had been experiencing powerful asthma attacks 2 to 3 times a month since his forties. He experienced mild attacks each evening or morning, and was being treated with intravenous injections of aminophylline and with oral and inhalation steroid hormones. He also used isoprenaline hydrochloride inhalation liquid.

Ever since sodium cromoglicate capsules had come out on the market, their use had resulted in fewer severe attacks, and this medication was used about once every 2 to 3 days. The patient experienced mild attacks in the morning or evening, which were alleviated by the inhalation of the sodium cromoglicate capsules, eliminating the need for aminophylline intravenous injections or oral steroid hormones. Ever since portable steroid hormone inhalants had come out on the market, the inhalation of beclometasone dipropionate or fluticasone propionate inhalant once or twice a day had resulted in the elimination of severe attacks and in fewer attacks in the evening or morning, but coughing sneezing, and the like were followed by mild attacks.

On Oct. 10, 2005, the patient started taking 1 mL of the inhalation epithelium-improving topical agent and 2 mL of sodium cromoglicate inhalation liquid by nebulizer 3 to 4 times a day, and discontinued inhalation steroid asthma treatment on Feb. 1, 2006. Mild wheezing in the chest which occurred after coughing and sneezing about once in the evening every 3 or 4 days was cured by one inhalation of procaterol hydrochloride. This was also effective for perennial allergic rhinitis, i.e., nasal obstruction, runny nose, itchy nose, and sneezing are also improved, and only some physiological sneezing with cold was. As of October 2006, the bronchial asthma attacks and allergic rhinitis which had been occurring since the patient's forties were cured by inhalation of the inhalation liquid of the invention and sodium cromoglicate, and the cough was cured by inhalation of procaterol hydrochloride once every 7 to 10 days as needed, without any use of steroids.

As of the beginning of November 2006, the patient's progress has been monitored with treatment using only the inhalation epithelium-improving topical agent (1 mL three times a day), without the use of sodium cromoglicate and procaterol hydrochloride. Until then, coughing and sneezing in the evening about once every 5 to 6 days had been followed by mild wheezing, but since the beginning of January 2007 there has been no wheezing in the chest after coughing and sneezing. As of June 2007, the patient has been free of bronchial asthma attacks while being treated with only the inhalation epithelium-improving topical agent. Pulmonary function tests before and after inhalation of the inventor's inhalation epithelium-improving topical agent also revealed mild improvement in vital capacity and forced vital capacity. The pulmonary function tests were performed in the absence of bronchial asthma and any abnormal chest findings.

The fact that the patient's progress was virtually free of the asthma attacks, which had occurred over the last 40 years, as a result of inhalation treatment with only the inventor's epithelium-improving topical agent, and without the use of anti-asthma medication such as steroids, bronchodilators, and anti-allergy agents, was attributed to the effect of the inventor's epithelium-improving topical agent.

(3) A 55-year old female had been officially designated patient of a pollution-related bronchial asthma since the age of 10, and had been treated with the following until her visit in May 1994:

Clenbuterol hydrochloride 4 T
Theophylline granules 200 2 T
Ambroxol hydrochloride 3 T
Fominoben hydrochloride 6 T
Triludan 2 T
Sodium cromoglicate inhalation 4 times
Fenoterol hydrobromide 4 times
Beclometasone dipropionate inhalation 4 times.

After that, she had been treated with the following, as the same before:

Theophylline 200 2 T
Pranlukast hydrate 4 T or Montelukast sodium 2 T
Procatelol hydrochloride 2 T
Huscode 6 T
Ambroxol hydrochloride 3 T
Sodium cromoglicate inhalation 4 times
Procatelol hydrochloride inhalation 2 breath 4 times
Beclometasone propionate inhalation 4 times or Fluticasone propionate inharation 2 times,
ten tablets of betamethasone 0.5 mg every two weeks for acute attacks.

Asthma attacks occurred every morning and occasionally in the afternoon. She had been treated with inhalation steroids, bronchodilators, and sodium cromoglicate inhalation, and had been hospitalized with a severe attack in August 2000.

On Apr. 21, 2006, the patient started taking 1 mL of the inventor's inhalation epithelium-improving topical agent and 2 mL of sodium cromoglicate inhalation liquid by ultrasonic nebulizer 2 to 3 times a day. The daily morning asthma attacks occurred once every 2 to 3 days instead of daily, symptoms were alleviated, and the patient tended to recover. Also, the amount of drugs used in that period was about 30% less than the average amount used in the previous 3 years. As of Sep. 15, 2006, there was no further need for the adrenocorticoid hormone, betamethasone.

It is noteworthy that, in the brief six-month period from April to October 2006, asthma attacks which had persisted for 45 years were alleviated, lower amounts of drugs were used, and steroid hormone medication in particular was discontinued. This effect was attributed to the effect of the inhalation epithelium-improving topical agent of the invention. The patient subsequently continued to use the inhalation epithelium-improving topical agent. As of August 2007, there were fewer asthma attacks. The patient experienced only mild asthma attacks due to differences in temperature when going in and out of the freezer at work or once in awhile in the morning. Pulmonary function tests before and after inhalation of the inhalation epithelium-improving topical agent also revealed mild improvement in vital capacity but no change in forced vital capacity. The pulmonary function tests were performed in the absence of bronchial asthma and any abnormal chest findings.

(4) 76-year old female: bronchial asthma, heart failure

The patient visited in February 2004, with a history of coughing, sputum, wheezing, and dyspnea since the summer of 2003. The patient presented with dry rales in the chest and edema of the lower extremities. Cigarettes: 20×30 years=600. The patient quit smoking in April 2004.

The patient was treated by internal use and topical application with:

Digoxin 1 to 0.5 T
Spironolactone 1 T
Diltiazem hydrochloride 3T
Ubidecarenone 3T
Ambroxol hydrochloride 1 T
Enalapril maleate 1T
Salmeterol xinafoate inhalation 2 times
Procatelol hydrochloride inhalation 2 breath by 4 times Starting on Oct. 19, 2005, the patient was treated by inhalation of 1 mL of the inhalation epithelium-improving topical agent and 2 mL of sodium cromoglicate twice a day. Procaterol hydrochloride was used for attacks of dyspnea. After about 2 months of use, the coughing, sputum, wheezing, dyspnea, edema, and dry chest rales were resolved. Progress was good, but the patient underwent surgery for colorectal cancer in June 2006. After being released from the hospital, the patient experienced only mild coughing, with no asthma attacks such as dyspnea. Pre-treatment and post-treatment pulmonary function tests, both during treatment with the inhalation epithelium-improving topical agent and in recent tests, revealed an increase in vital capacity and improvement in force vital capacity, despite the two months of hospitalization, surgery, and poor health involving the colorectal cancer which took place between the pulmonary function tests. The pulmonary function tests were performed in the absence of bronchial asthma and any abnormal chest findings.

(5) 7-year old male: bronchial asthma

The patient had experienced occasional asthma attacks since the age of 3 years, and had experienced nasal discharge, coughing, and dyspnea the day before. At the time of the patient's visit, chest auscultation revealed pronounced dry rales. After 10-min inhalation treatment with the inhalation epithelium-improving topical agent by ultrasonic nebulizer, chest auscultation revealed virtually no dry rales, the dyspnea had abated, and the cough and nasal discharge were alleviated.

(6) Female (A) 1 year, 5 months: bronchial asthma

The patient was by nature susceptible to catching cold and had occasionally experienced asthma attacks. At the time of the patient's visit, chest auscultation revealed pronounced dry rales. After 10-min inhalation treatment with the inhalation epithelium-improving topical agent by ultrasound nebulizer, chest auscultation revealed virtually no dry rales, the dyspnea had abated, and the cough and nasal discharge were alleviated. The patient recovered after three treatments with the epithelium-improving topical agent over a period of 3 days.

(B) At 1 year and 6 months of age, the patient experienced wheezing and symptoms of a cold such as nasal discharge and cough starting the day before the visit. At the time of the patient's visit, chest auscultation revealed pronounced dry rales. Wheezing improved and the patient fell asleep 30 min after 10-min of treatment with the inhalation epithelium-improving topical agent by ultrasonic nebulizer. The patient visited again in the early evening, with moderate dry rales, and the same 10-min inhalation treatment was performed. That night wheezing was mild, but the patient slept well. After another 10-min treatment with the inhalation epithelium-improving topical agent by ultrasonic nebulizer on the following morning, the asthma attack cleared up, leaving the patient in good health. During that time, the patient used a tulobuterol patch, and was given cefpodoxime proxetil for tonsillitis.

The improvement in dyspnea and the diminishment of the dry rales about 30 min after 10-min inhalation treatment with the inhalation epithelium-improving topical agent in the cases in (5) and (6) above were attributed to the fast-acting effect of the inhalation epithelium-improving topical agent for bronchial asthma. Based on its composition, the inhalation epithelium-improving topical agent may serve as an excellent medication for treatment of bronchial asthma in the future without resulting in side-effects.

(7) 5-year old male: bronchial asthma, atopic dermatitis

Since the age of 1 years and 7 months, the patient had been experiencing asthma attacks, as well as atopic dermatitis, and had experienced a powerful asthma attack at the age of 1 year and 8 months. Symptoms were alleviated by short-term treatment with the adrenocorticoid hormone medication, betamethasone, and the bronchodilator tulobuterol patch. The patient was subsequently susceptible to colds, and visited 6 to 9 times per month. Chest auscultation occasionally revealed dry rales. Strong asthma attacks were resolved by 5-min treatment with betamethasone phosphate and sodium cromoglicate inhalation liquid using an ultrasonic nebulizer, as well as a tulobuterol patch. Since October 2005, the patient has been treated 88 times over a period of 1 year and 1 month by 5-min ultrasonic nebulizer inhalation therapy with 1.0 mL inhalation epithelium-improving agent (diluted 3-fold with purified water) and 2 mL sodium cromoglicate inhalation liquid. From November 2006 to July 2007, the patient was treated 44 times by 5 to 10 min of ultrasonic nebulizer inhalation therapy with just the inhalation epithelium-improving agent. During that time, the patient often visited because of a cold, but suffered no asthma attacks, and chest auscultation revealed dry rales only twice. Atopic dermatitis also occasionally developed but was cured by the application of the topical agent in Example 2. The patient has been visiting less often recently. In many cases, bronchial asthma which develops around 2 years of age becomes worse with each subsequent attack and often becomes a hardship. For strong attacks, short-term treatment with adrenocorticoid hormone medication, subsequent inhalation therapy with betamethasone phosphate and sodium cromoglicate inhalation liquid, further inhalation therapy with the inhalation epithelium-improving topical agent and sodium cromoglicate inhalation liquid, and recent treatment with just the inhalation epithelium-improving topical agent have resulted in no further asthma attacks. This was considered a favorable case showing good therapeutic efficacy.

Figure 2:
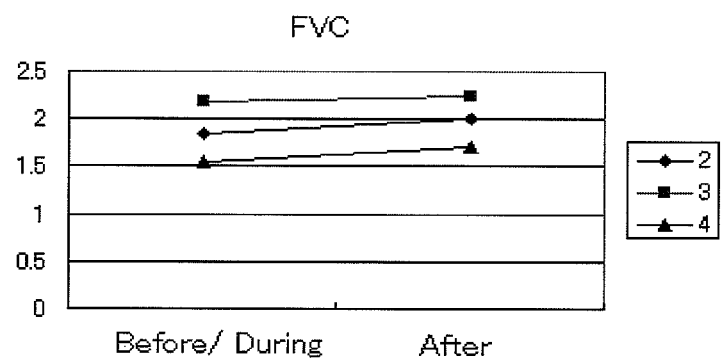

Table 1 shows the efficacy of the inhalation epithelium-improving topical agent for bronchial asthma. Pulmonary function test results are given in Table 2 and FIGS. 1 and 2. The tables of the pulmonary function tests give the results before and during inhalation therapy, and the starting time and duration of the inhalation therapy with the inhalation epithelium-improving topical agent are given in years and months.

TABLE 1

Efficacy of the inhalation epithelium-improving topical agent for bronchial asthma

| | Sex | Age | Onset Histry | Disease | Steroid Internal use/ Topical appli. | Bronchodilator | Antiallergic Drug | Inhalation of This Agent times/day | Term | Efficacy |
|---|---|---|---|---|---|---|---|---|---|---|
| 1 | ♀ | 63 | 4 years | Bronchial Asthma, Allergy Rhinitis | +/+ Ax/ax | + | + | 1 to 2 | 1 y | Quite-efficacious |
| 2 | ♂ | 80 | 40 years | Bronchial Asthma, Allergy Rhinitis | +/+ Ax/ax | + | + | 3 to 4 | 1 y 4 ms | Quite-efficacious |
| 3 | ♀ | 55 | 45 years | Bronchial Asthma | +/+ Ax/ tapering | + | + | 1 to 2 | 10 ms | Quite-efficacious |
| 4 | ♀ | 76 | 6 months | Bronchial Asthma, Cardiac Arrest | −/− | + | + | 2 to 3 | 1 y 2 ms | efficacious |
| 5 | ♂ | 7 | 4 years | Bronchial Asthma | −/− | − | − | 1 | 1 d | Quite-efficacious |
| 6 | ♀ | 1.5 | 1 year | Bronchial Asthma | −/− | + | − | 1 to 2 | 3 ds/2 times | Quite-efficacious |
| 7 | ♂ | 5 | 3 years and 6 months | Bronchial Asthma | +/− Ax | + | − | 1 | 1 y 10 ms | efficacious |

TABLE 2

Pulmonary function tests

| (2) | Before inhalation | | | During inhalation after 1 year + 2 months | | |
|---|---|---|---|---|---|---|
| VC | 2.44 | 3.01 | 81% | 2.80 | 2.99 | 93% |
| FVC | 1.85 | 3.01 | 61% | 2.01 | 2.99 | 67% |
| FEV 1% | 77.84 | | | 78.10 | 61.95 | |
| MMF | 1.21 | 2.53 | 48% | 1.32 | 2.49 | 53% |

| (3) | Before inhalation | | | During inhalation after 8 months | | |
|---|---|---|---|---|---|---|
| VC | 1.96 | 2.56 | 77% | 2.40 | 2.56 | 93% |
| FVC | 2.18 | 2.56 | 85% | 2.24 | 2.56 | 87% |
| FEV 1% | 73.85 | | | 69.64 | 77.76 | 89% |
| MMF | 1.32 | 2.88 | 46% | 1.05 | 2.88 | 36% |

| (4) | During inhalation after 4 months | | | During inhalation after 1 year + 4 months | | |
|---|---|---|---|---|---|---|
| VC | 1.84 | 2.19 | 84% | 2.33 | 2.16 | 108% |
| FVC | 1.54 | 2.19 | 70% | 1.71 | 2.16 | 79% |
| FEV 1% | 69.48 | | | 58.11 | | |
| MMF | 0.83 | 2.06 | 40% | 0.54 | 2.00 | 27% |

(IV) The Effect on Sexual Sensation was Investigated in 7 Males and 3 Females.

The application of the sexual sensation-improving topical agent by the inventor 1 to 4 times a day for 1 to 2 months or more on the glans penis, clitoris, or vagina resulted in improved sensation and better sexual sensation only in individuals experiencing a loss of sexual sensation due to aging or various other causes. Out of the 10 subjects, sexual sensation was dramatically improved in 3 males and 1 female, mildly improved in 1 male and 1 female, and better than before in 1 female, but had no effect in 3 males who did not suffer from a loss of sexual sensation.

1. A 60-year old male applied the medication for about a month and a half. Whereas recently he had engaged in intercourse about once a month without much interest, he was now more interested and had increased to twice a month. The patient is continuing to apply the medication.

2. A 76-year old male applied the medication about 3 to 4 times a day for about 1 month, resulting in better sensation in the glans penis, a shorter period of sexual intercourse, the lack of any need for pausing, improved sexual sensation, and the ability to achieve a sense of penile presence. The patient is continuing to apply the medication.

3. A 55-year old male was younger, with less diminished sexual sensation to begin with, and the application therefore was not found to improve sexual sensation. The patient is continuing to apply the medication.

4. A 68-year old male applied the medication for about 2 months, resulting in significantly improved sexual sensation, better urination, and better sensation in the glans penis. The patient is continuing to apply the medication.

5. A 59-year old male applied the medication for about 2 months, but there was no effect since he was younger and suffered from less diminished sexual sensation. The patient is continuing to apply the medication.

6. A 60-year female applied the medication for about 2 months. Although the patient had not experienced problems in sexual sensation to begin with, she reported improvement. The patient is continuing to apply the medication.

7. A 60-year female experienced pain during sexual intercourse. Application of the medication for 2.5 months resulted in less pain, with mild improvement in sexual sensation, but further use was needed in order to determine the effects. The patient is continuing to apply the medication.

8. A 51-year old female applied the medication for about 2 months. Despite little loss of current sexual sensation, the patient experienced better sexual sensation, with better genital lubrication and softness. The patient is continuing to apply the medication.

9. A 55-year old male applied the medication for about 2 months. Although there were no problems to begin with, there was mild improvement in sexual sensation. The patient is continuing to apply the medication.

10. A 60-year old male applied the medication for about 2 months, but since he reported no problems with sexual sensation to begin with, no effect could be confirmed. The patient is continuing to apply the medication.

(V) Hair Growth Effect

Although limited to 7 cases, 3 or more months of application in which the epithelium-improving topical agent was lightly rubbed into the skin around white hair was found to result in the growth of black, melanin pigment-containing hair and darker scalp hair overall. The cream may stimulate melanocytes, but further study is required.

(1) A 77-year old female applied the epithelium-improving cream, lightly rubbing it into the scalp. In about 6 months, she noticed the growth of fine dark hair ranging from 5 millimeters to 1 centimeter. Very fine dark hairs were found among the white hair (the white hair had been dyed brown at that time). After 2 years and 5 months, it was immediately evident that the dark hair had grown to between 5 and 10 cm and that the number of strands had increased, indicating obvious hair growth. During this period, the patient underwent surgery for colorectal cancer. The patient reported this during the second year that the epithelium-improving cream was being applied.

(2) A 70-year old female applied the epithelium-improving cream to her scalp for about 11 months. Before applying the cream, the patient photographed here scalp as a joke about applying the cream to her scalp. Another photograph was taken after 11 months, and comparison of the photographs revealed that white hair at the crown of the head had darkened. The cream was also applied to the eyelashes at the same time, and the patient noticed her eyebrows were darker overall after 11 months. The patient stopped dyeing her white hair (brown), and is currently further applying the epithelium-improving cream.

(3) For about 2 years or more, a 97-year old female applied the epithelium-improving cream as far as the hairline when applying it to the face. The patient reported that, about 8 months previously (January 2007), dark hair had grown in white-haired areas and that her daughter had noticed. Fine dark hair about 3 to 5 cm was visible in white-haired areas at the hairline.

(4) A 75-year old woman had been applying the epithelium-improving cream because her hairline was dyed a fair-haired color. About 1 month before (July 2007), she noticed 10 to 20 strands of dark hair about 1 cm growing in white-haired areas at the hairline. After about 1 week, they fell out. This was reported by the individual. The patient is currently continuing to lightly rub the epithelium-improving cream into the hair line in the hope of again growing dark hair.

(5) In the third month of applying the epithelium-improving cream, a 78-year old female noticed fine dark hair about 5 mm growing in white-haired areas of the hair line, and is continuing to apply the cream.

(6) After an 81-year old male had been applying the epithelium-improving cream for 2 years, the growth of dark hair made the white hair on the sides of his head less noticeable, changing the white hair to a fair-haired color. Dark hair also grew in the thin, short white hair at the crown of the head, and bald areas were covered a bit by dark hair. After a year of application, spots of dark hair had grown on the inside (nose side) of the eyebrows, and by the second year had grown into dark hair about 1 millimeter.

(7) The hairline of a 56-year old male had turned noticeably white. When he had been applying the epithelium-improving cream for 5 months, his daughter remarked that the white hair had been dyed a fair color, indicating that the growth of the dark hair made the white hair less noticeable. When the cream had been being applied for 8 months, more dark hair had grown, making the white hair less noticeable.

Summary of Effects (I) The invention is effective for the pain, redness, and swelling of the gums in gingivitis, and for loose teeth in periodontitis, with some teeth being fully restored to their original condition. Individuals in whom the effect on pain, redness, and swelling was most rapid recovered in about half a day, most individuals recovered in 3 to 4 days, and recovery took 7 days in individuals who took the longest time to recover. Those who experienced rapid pain relief were very delighted. There was not much need for antibiotics or anti-inflammatory analgesics for the pain, redness, and swelling, and the local lymph gland swelling and pain were cured without the use of antibiotics in case (1).

There was no recurrence of gingivitis or periodontitis after about one year or more in the six subjects (1), (2), (3) (6), (7), and (10) who continued interdental application of the gingivitis and periodontitis epithelium-improving agent using an interproximal brush for the purpose of investigating the effect in preventing gingivitis and periodontitis. Further research is needed.

(II) The invention is fast-acting on the cold symptoms of nasal discharge, nasal obstruction, cough, and sore throat, and shows effects immediately after inhalation of the inhalation epithelium-improving topical agent by ultrasonic nebulizer. In this test example, the results of a single nebulizer inhalation treatment prior to taking cold medication suggest that 3 to 4 times a day, if possible, may be even more effective. Inhalation did not result in side effects.

(III) Effect on Bronchial Asthma

The inhalation liquid of the invention is believed to have been very effective for bronchial asthma attacks in all cases of bronchial asthma. The fact that the interruption of treatment with the inhalation topical agent resulted in bronchial asthma attacks in case (1) shows that the inhalation topical agent is effective for bronchial asthma. It is also noteworthy that pulmonary function tests revealed improvement in vital capacity in 3 cases. The fact that patients showed good progress with lower doses of steroid hormone medication, or even none at all, during the treatment of bronchial asthma with the inventor's inhalation liquid is ground-breaking in terms of bronchial asthma therapy. Although more cases are needed, the rapid improvement in chest findings and resolution of dyspnea as a result of about 10 minutes of ultrasonic nebulizer inhalation therapy in cases (7) and (8) show this to be an exceptional therapeutic method for the treatment of bronchial asthma. Similar to the effect on symptoms of inflammation of the nasal mucosa, which include itching sensation, sneezing, and nasal discharge, such as in the common cold and allergic rhinitis, the above is attributed to the effect on the airway and bronchi by the same mechanism of action against asthma-induced inflammation of the airway and bronchi, edema of the airway mucosa, smooth muscle spasms, and airway obstruction caused by increased secretion. Inhalation did not result in side effects.

(IV) Effect on genital sexual sensation: This is attributed to regeneration and stimulation of sexual sensation receptors in the genital epithelia which have become weakened as a result of aging or other reasons, and is effective for individuals with diminished sexual sensation. Application resulted in virtually no side effects.

(V) Hair growth effect: Although the small number of cases will necessitate further study, the growth of dark hair in white-haired areas was found.

The inventor's epithelium-improving topical agent based on coenzyme Q10, cysteine, Vitamins A, C, and E, and extract of inflamed skin from domestic rabbits inoculated with vaccinia virus, which have the four exceptional functions on skin of making skin smoother, whiter, and rosy complexion, and of being effective on wrinkles, is an utterly novel epithelium-improving therapeutic agent that has effects not previously disclosed, that is, effects in improving gingivitis and periodontitis, the common cold and bronchial asthma, and sexual sensation, and in growing melanin pigmented hair, by ultrasonic nebulizer inhalation or spraying into the ear, nasal cavity, paranasal sinuses, oral cavity, pharynx, tonsils, larynx, trachea, bronchi, or alveolar epithelia, by interdental application using an interproximal brush, or by application to the genital epithelia or white-haired skin.

The efficacy noted in detail above will require further histological study. Although the details are not yet known similar to the exceptional effect of the inventor's topical agent on hair and skin, the invention may, it has the effect of rehabilitating epithelia by stimulating and regenerating epithelial function of the epithelia in the ears, nasal cavity, paranasal sinuses, oral cavity, pharynx, tonsils, larynx, trachea, bronchi, or alveoli which have been compromised by external stimuli, microbial infection, allergic response, aging, pathology, or the like, and in which the inherent defensive mechanism of the body against foreign attacks has been compromised.

BRIEF DESCRIPTION OF THE DRAWINGS

FIG. 1 is a graph showing variation of pulmonary capacity from bronchial asthma patients inhaling the liquid epithelium-improving agent by ultrasonic nebulizer. This shows variation of pulmonary capacity before inhalation or during inhalation to after 4 months to 1 year and 4 months of inhalation, and increasing for 3 patients.

FIG. 2 is a graph showing variation of forced vital capacity from bronchial asthma patients inhaling the liquid epithelium-improving agent by ultrasonic nebulizer. This shows variation of forced vital capacity before inhalation or during inhalation to after 4 months to 1 year and 4 months of inhalation, and no change for 3 patients.

*4 yellow line shows a patient which was given a colon cancer surgery during measurement.

DESCRIPTION OF THE NUMERALS

Before: First pulmonary function tests before inhalation 2, 3

During: First pulmonary function tests during inhalation 4

After: Second pulmonary function tests after inhalation

L: 1000 mL

VC: breathing capacity, FVC: forced expiratory volume, FVC 1.0%: forced expiratory volume in 1 second as percent of FVC, MMF: maximal mid-expiratory flow

DETAILED DESCRIPTION OF THE PREFERRED EMBODIMENTS

The coenzyme Q10 used in the present invention has biological activity as a coenzyme, is a constituent of mitochondrial electron transport systems, and serves to produce energy as an activator in the biosynthesis of ATP. Coenzyme Q10 is a ubiquinone (2,3-dimethoxy-5-methyl-6-polyprenyl-1,4-benzoquinone) specific to humans, with 10 side chain isoprenoid units, and is referred to as ubidecarenone or coenzyme UQ 10. This is an odorless and tasteless yellow to orange-yellow crystalline powder with a molecular weight of 863.36 and a melting point of about 48 degrees. It is freely soluble in ether, and decomposes and darkens on exposure to light. Although the amount in which the coenzyme Q10 is added is not particularly limited, the amount is preferably 0.001 to 4.0 weight parts, and more preferably 0.03 to 1.2 weight parts. A concentration greater than this cannot be expected to result in any better epithelial effects, whereas a concentration below this range will not result in beneficial epithelial effects.

The cysteine used in the present invention functions as an SH donor in the metabolic system of the living body and acts as an SH enzyme activator. It has cutaneous metabolism-normalizing action, antiallergic action, and detoxifying action. The cysteine or derivatives thereof are not particularly limited, although cystine and the like are examples of L-cysteine derivatives including N-acetyl-L-cysteine, L-homocysteine, L-cysteic acid, L-homocysteic acid, L-cysteine sulfinic acid, S-sulfino-L-cysteine, S-sulfo-L-cysteine, cystine and the like. Examples of salts of cysteine and its derivatives include mineral acid salts such as a hydrochloride, a nitrate salt, a hydrosulfate, and alkali metal salts and alkaline earth metal salts such as a sodium salt, calcium salts and magnesium salts. L-cysteine is preferred among L-cysteine, derivatives thereof, or their salts in the present invention.

The Vitamin A used in the present invention has action in improving retinal adaptation to the dark, as well as action in improving abnormal drying and keratinization of the skin and mucosa and action in enhancing resistance to disease. The Vitamin A is not particularly limited, but specific examples include retinol, dehydroretinol, retinol acrtate, retinole palmitate, and the like, as well as derivatives thereof. Examples of retinoids, which are related compounds of retinol, include derivatives of retinol, retinol ester, retinoic acid or the like and derivatives thereof. Retinol and the derivative retinol palmitate are preferred in the present invention.

The ascorbic acid or salt thereof used in the present invention was initially believed to have antiscorbutic action, but was also found to be essential to the formation and maintenance of intercellular matrix and collagen in the living body, as the administration of ascorbic acid was found to increase collagen. It is also involved in melanin pigment production, inhibiting the production of melanin from tyrosine. It also has action in converting the oxidized type dark melanin into the reduced type light melanin, and prevents dyspigmentation. It is also an important substance involved in protein metabolism and endocrine function. The Vitamin C is not particularly limited. Specific examples include L-ascorbic acid, and examples of derivatives or salts thereof include mineral acid salts such as a hydrochloride, a nitrate salt, a hydrosulfate, and alkali metal salts and alkaline earth metal salts such as a sodium salt, calcium salts and magnesium salts. Examples of L-ascorbic acid and derivatives or salts thereof include L-ascorbic acid salts such as L-ascorbic acid, sodium L-ascorbate, potassium L-ascorbate, calcium L-ascorbate, magnesium L-ascorbate; L-ascorbic acid monoalkyl or monoalkenyl ester such as L-ascorbic acid monostearate, L-ascorbic acid monopalmitate, L-ascorbic acid monooleate; L-ascorbic acid dialkyl or dialkenyl ester such as L-ascorbic acid distearate, L-ascorbic acid dipalmitate, L-ascorbic acid dioleate; L-ascorbic acid trialkyl or trialkenyl ester such as L-ascorbic acid tristearate, L-ascorbic acid tripalmitate, L-ascorbic acid trioleate; L-ascorbic acid sulfates such as L-ascorbyl sulfate, sodium L-ascorbyl sulfate, potassium L-ascorbyl sulfate, magnesium L-ascorbyl sulfate, calcium L-ascorbyl sulfate; L-ascorbyl phosphate such as L-ascorbyl phosphate, sodium L-ascorbyl phosphate, potassium L-ascorbyl phosphate, magnesium L-ascorbyl phosphate, calcium L-ascorbyl phosphate; ascorbic acid glycosides such as L-ascorbic acid glycoside. L-ascorbic acid is preferred among the L-ascorbic acid, derivatives thereof, or their salts in the present invention.

Vitamin E is related to pregnancy and birth, and is referred to as an elixir. It serves to dilate the peripheral blood vessels and improve blood circulation. The two ingredients Vitamin E and coenzyme Q10 are known as very closely related components that together regulate electron transport to inhibit oxidation in the body and the like. The Vitamin E is not particularly limited. Specific examples include tocopherol succinate, tochpherol acetate, tocopherol nicotinate or derivative thereof, and the like. Tocopherol nicotinate are preferred in the present invention as Vitamin E and its derivative.

The extract of inflamed skin from domestic rabbits inoculated with vaccinia virus is an essential ingredient of the present invention, is effective for dermatological pruritus, coldness, and paresthesia, and for pain such as lower back pain and neuralgia, and also has antiallergic action.

Examples of antiallergy agents include azelastine hydrochloride, epinastine hydrochloride, ozagrel hydrochloride, olopatadine hydrochloride, cetirizine hydrochloride, fexofenadine hydrodhloride, loratadine and the like. Loratadine is an antiallergy drug that has histamine H1 receptor antagonism as well as action in inhibiting antigen provocation, is effective for pruritus in dermatological disease, and has antiallergic action. Loratadine is preferred in the present invention.

The present invention is illustrated by, but is not limited to, the following example.

EXAMPLE

Example 1

Liquid epithelium-improving agent for inhalation by ultrasonic nebulizer to treat the common cold and bronchial asthma Preparation of epithelium-improving agent in the form of an application liquid for gingivitis and periodontitis An epithelium-improving agent in the form of an inhalation liquid and a liquid epithelium-improving agent for the treatment of gingivitis and periodontitis was prepared with the following composition in the usual manner.

tocopherol nicotinate 200 mg (trademark NE soft capsules) 20 pills (not including soft capsule)
retinol palmitate preparation (trademark Chocola A Drops) 30 mL
ubidecarenone tablets 10 mg (trademark Adelir tablets 10 mg) 300 tablets
L cysteine powder 32% (trademark Hythiol powder 32%) 15 g ascorbic acid (Japanese Pharmacopoeia) 20 g
extract of inflamed skin of domestic rabbits inoculated with vaccinia virus (trademark Nabutopin) 7.2 U 6 mL
loratadine tablets 10 mg (trademark Claritin tablets 10 mg) 20 tablets purified water 500 mL.

Example 2

Cream epithelium-improving agent for improvement of sexual sensation and hair growth application An epithelium-improving agent in the form of a topical application was prepared with the following composition in the usual manner.

tocopherol nicotinate 200 mg (trademark NE soft capsules) 20 pills (not including soft capsule)
retinol palmitate preparation (trademark Chocola A Drops) 30 mL
ubidecarenone tablets 10 mg (trademark Adelir tablets 10 mg) 300 tablets
L cysteine powder 32% (trademark Hythiol powder 32%) 15 g ascorbic acid (Japanese Pharmacopoeia) 20 g
extract of inflamed skin of domestic rabbits inoculated with vaccinia virus (trademark Nabutopin) 7.2 U 6 mL
loratadine tablets 10 mg (trademark Claritin tablets 10 mg) 20 tablets
liquid paraffin (Japanese Pharmacopoeia) 50 mL
hydrophilic ointment (Japanese Pharmacopoeia) 500 g.

The invention claimed is:

1. A method for promoting growth of melanin pigment-containing black hair from areas with white hair, comprising administering to a subject, an agent containing coenzyme Q10, cysteine, vitamins, and an extract of inflamed skin from domestic rabbits inoculated with vaccinia virus, in a therapeutically effective amount to promote the growth of melanin pigment-containing black hair.

2. A method as claimed in claim 1, wherein the cysteine is L-cysteine or derivatives thereof.

3. A method as claimed in claim 1, wherein the vitamins comprises Vitamin A, C, E or derivertives thereof.

4. A method as claimed in claim 3, wherein the Vitamin A is retinole palmitate or derivatives thereof.

5. A method as claimed in claim 3, wherein the Vitamin C is ascorbic acid or derivatives thereof.

6. A method as claimed in claim 3, wherein the Vitamin E is tocopherol or derivatives thereof.

7. A method as claimed in claim 3, wherein the Vitamins are a mixture of retinole palmitate or derivatives thereof, ascorbic acid or derivatives thereof and tocopherol or derivatives thereof.

8. A method as claimed in claim 1, wherein the agent comprising;
coenzyme Q10 (0.03 to 1.2 weight parts),
L-cysteine (0.48 to 2.4 weight parts),
Vitamin A (0.06 to 0.36 weight parts),
Vitamin C (2.0 to 8.0 weight parts),
Vitamin E (0.4 to 1.6 weight parts),
extract of inflamed skin from domestic rabbit inoculated with vaccinia virus 3.6 to 14.4 units, 3 ml to 12 ml, (0.6 to 2.4 weight parts) and
liquid paraffin (4.4 to 13.2 weight parts) relative to 500 weight parts hydrophilic ointment in the form of cream for application to hair growth.

9. A method as claimed in claim 1, wherein the agent comprising;
coenzyme Q10 (0.03 to 1.2 weight parts),
L-cysteine (0.48 to 2.4 weight parts),
Vitamin A (0.06 to 0.36 weight parts),
Vitamin C (2.0 to 8.0 weight parts),
Vitamin E (0.4 to 1.6 weight parts),
extract of inflamed skin from domestic rabbit inoculated with vaccinia virus 3.6 to 14.4 units, 3 ml to 12 ml, (0.6 to 2.4 weight parts) and
loratadine (0.01 to 0.12 weight parts) per 500 weight parts purified water for application to hair growth.

* * * * *